United States Patent [19]
Farin et al.

[11] Patent Number: 5,776,092
[45] Date of Patent: Jul. 7, 1998

[54] MULTIFUNCTIONAL SURGICAL INSTRUMENT

[75] Inventors: Gunter Farin, Tubingen; Klaus Fischer, Nagold-Emmingen; Dieter Muller, Wangen, all of Germany

[73] Assignee: Erbe Elektromedizin GmbH, Tubingen, Germany

[21] Appl. No.: 408,311

[22] Filed: Mar. 22, 1995

[30] Foreign Application Priority Data

Mar. 23, 1994 [EP] European Pat. Off. .......... 94 104 568.4

[51] Int. Cl.$^6$ ............................................ A61B 17/20
[52] U.S. Cl. ........................ 604/22; 604/280; 606/37
[58] Field of Search ........................... 604/22, 30, 31, 604/39, 40, 280; 606/37, 39, 40, 50

[56] References Cited

U.S. PATENT DOCUMENTS

| | | |
|---|---|---|
| 4,931,047 | 6/1990 | Broadwin et al. . |
| 5,015,227 | 5/1991 | Broadwin et al. . |
| 5,098,430 | 3/1992 | Fleenor . |
| 5,195,958 | 3/1993 | Phillips . |
| 5,304,176 | 4/1994 | Phillips . |
| 5,306,238 | 4/1994 | Fleenor . |
| 5,324,254 | 6/1994 | Phillips . |

FOREIGN PATENT DOCUMENTS

| | | |
|---|---|---|
| 0310431 | 5/1989 | European Pat. Off. . |
| 0463363 | 2/1992 | European Pat. Off. . |
| 0547772 | 6/1993 | European Pat. Off. . |
| WO9113593 | 9/1991 | WIPO . |

OTHER PUBLICATIONS

"Pneumatically Controlled Bipolar Cutting Instrument" by G. Farin; Endoscopic Surgery And Allied Technologies, No. 2, vol. 1, Apr. 1993.

*Primary Examiner*—Robert A. Hafer
*Assistant Examiner*—Perry E. Van Over
*Attorney, Agent, or Firm*—St. Onge Steward Johnston & Reens

[57] ABSTRACT

Multifunctional instrument for ultrasound surgery having an applicator 2 for a dissection of biological tissue, as well as a device for cutting and/or coagulating of the tissue. At the instrument end separate from the ultrasound applicator 2 at least one RF-current applicator 16 or a laser applicator 15 is arranged in a lateral distance from the distal end 3 of the ultrasound applicator 2, whereby an adjustable arrangement is provided. Each applicator 2, 6, 15 is movable in longitudinal direction in a common applicator housing 9. The applicators may be provided in a revolver unit, which is arranged at the instrument and can be rotated around its longitudinal axis.

17 Claims, 6 Drawing Sheets

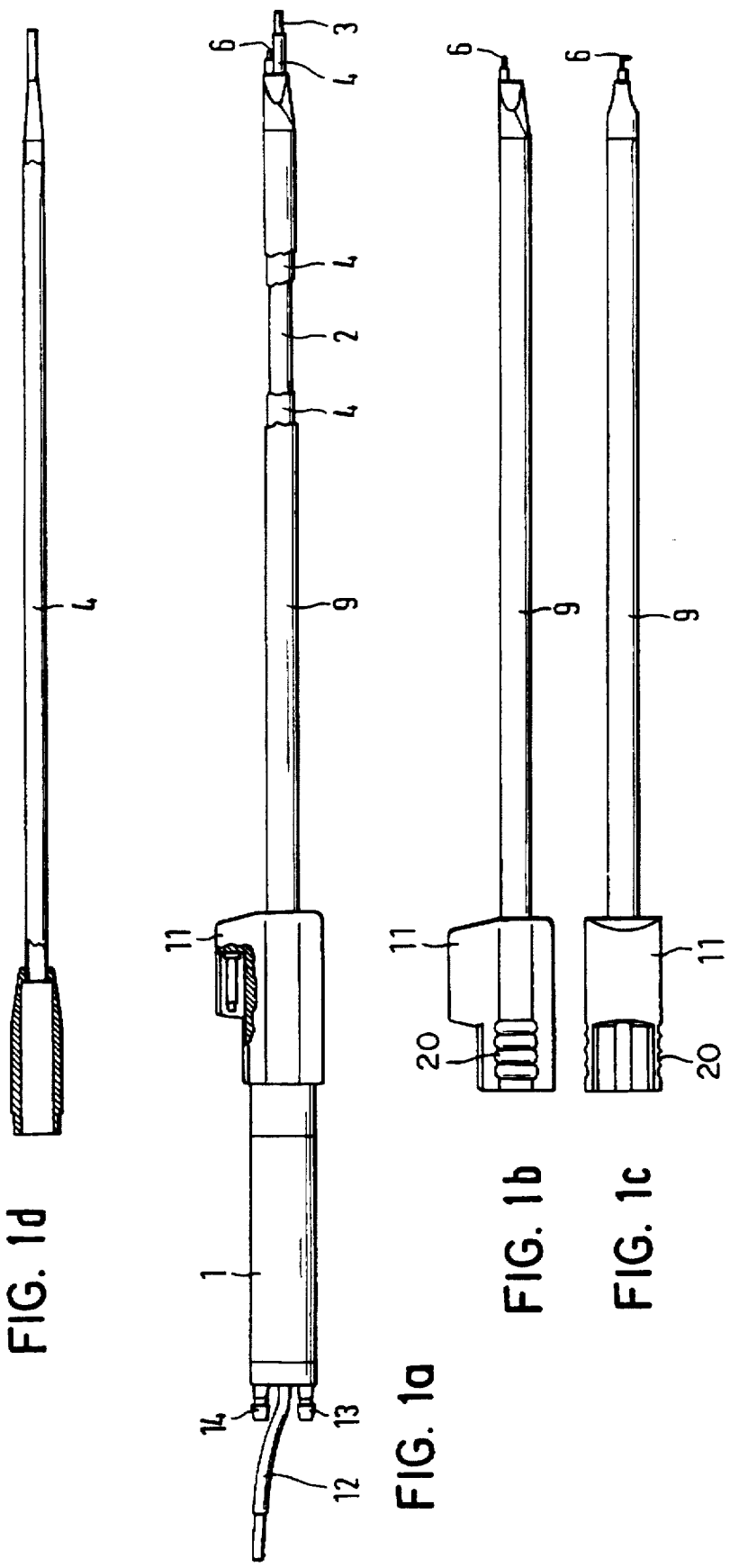

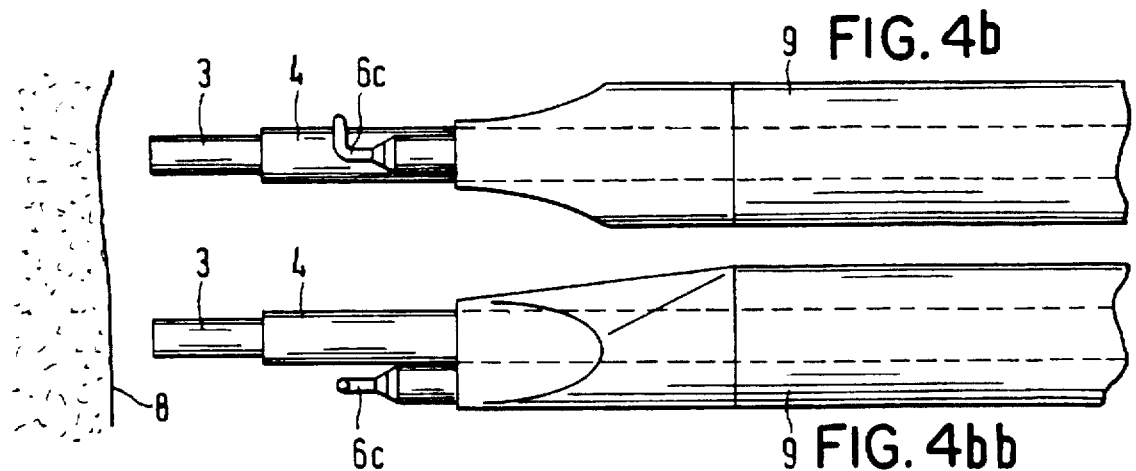
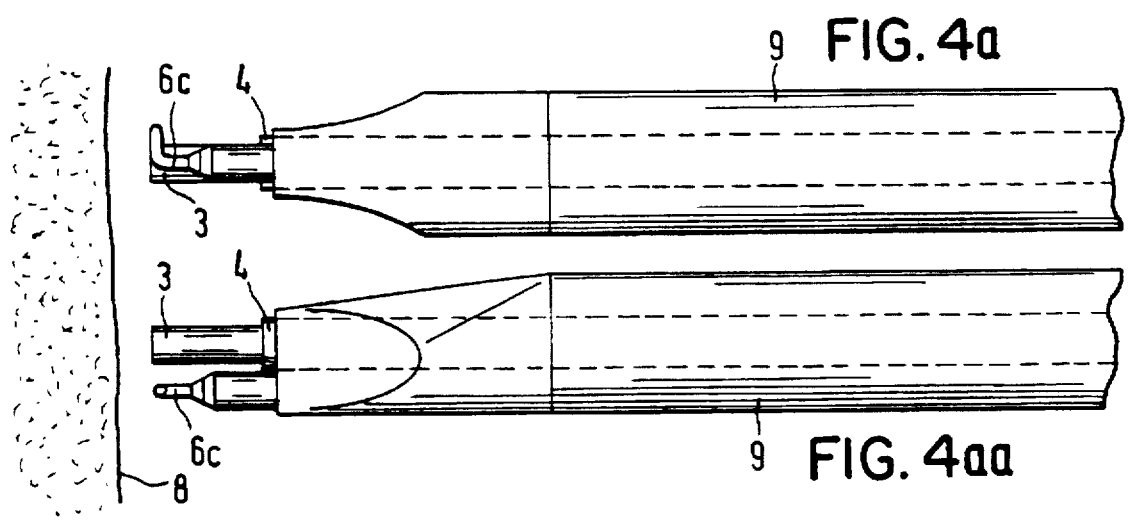
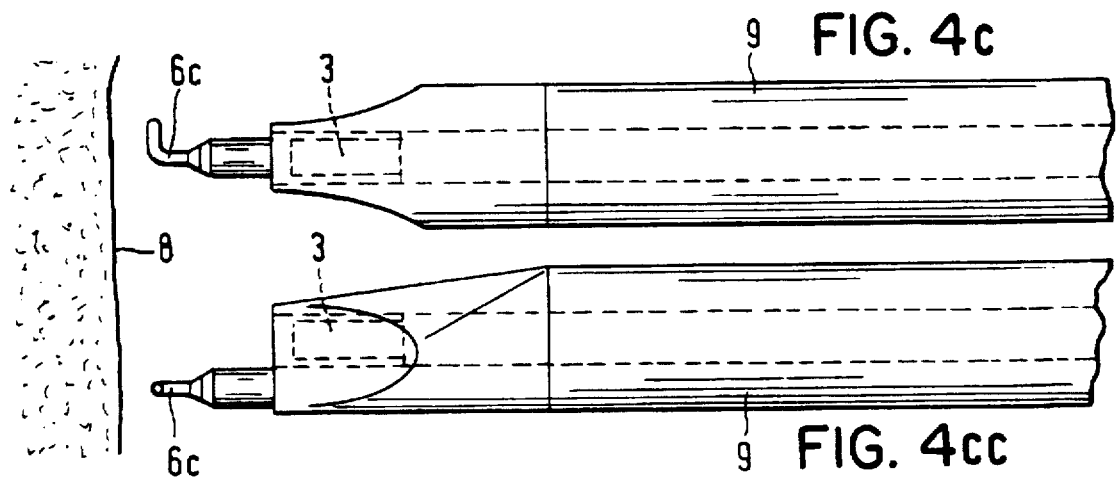

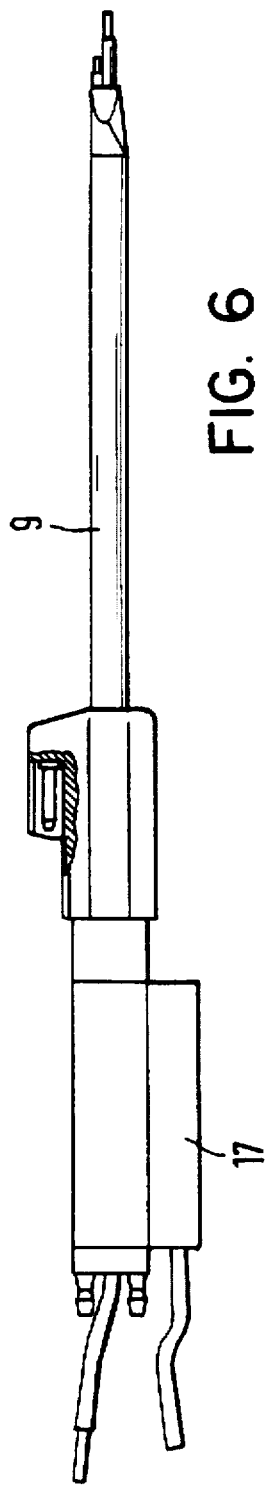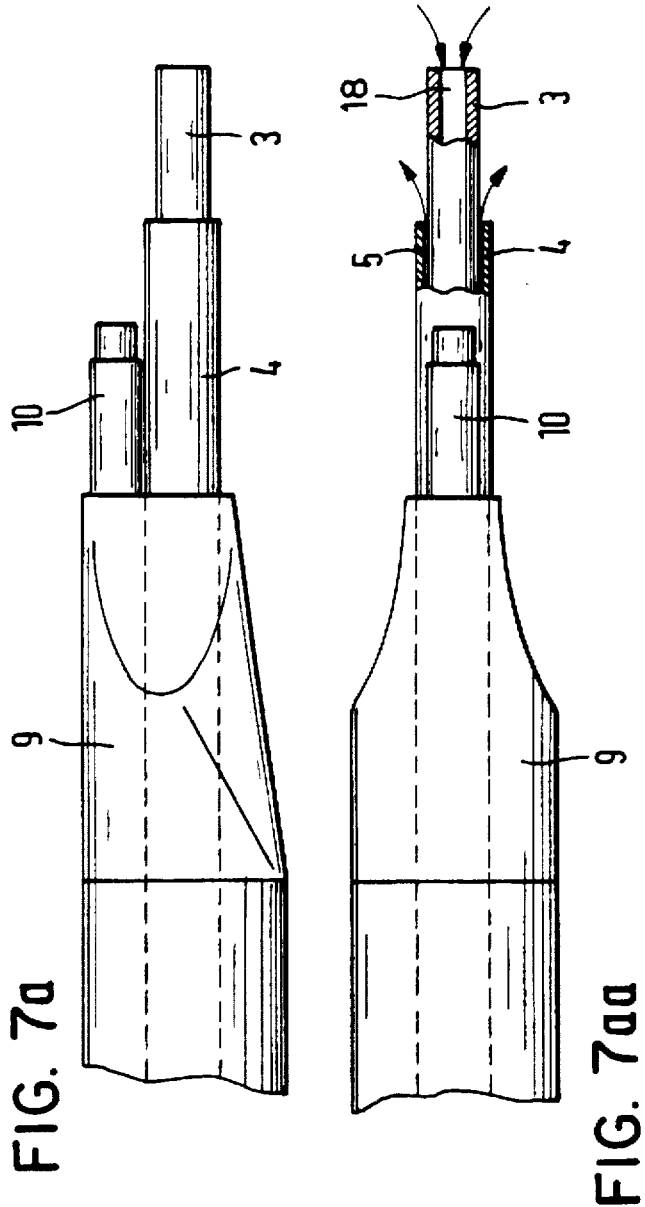

MULTIFUNCTIONAL SURGICAL INSTRUMENT

FIELD OF THE INVENTION

The present invention relates to surgical methods and devices for ultrasonically fragmenting and aspirating, and electrosurgically coagulating and electrosurgically cutting tissue at an operative site on a patient.

BACKGROUND OF THE INVENTION

Ultrasonic surgery is a method for tissue-selective dissections. RF-surgery is a non-selective method whereby all kinds of tissue (except bones) can be cut. Ultrasonic surgery does not effect hemostasis. On the other hand, RF-surgery can be successfully used for hemostasis. The combined use of ultrasonic surgery and of RF-surgery allows supplementing the properties of both methods, especially in the case of endoscopic operations, whereby the operation techniques can be improved or new techniques become possible, which otherwise could not be performed.

The tissue specific selectivity of a dissection with ultrasound results on the one hand from the different resistance to tearing as well as from the relative water content of the different tissues, and on the other hand from the power density of the ultrasound in the tissue. Tissue with low resistance against tearing and relative high water content (e.g. parenchyma) can be fragmented even with a lower power density of the ultrasound. Tissue with high resistance against tearing and/or low water content (e.g. connective tissue, stroma) requests a relatively high power density of the ultrasound. The dissection by ultrasound is appropriate therefore especially for a selective preparation of tissue structures meeting the conditions of anatomy e.g. for unmasking of organs or vessels surrounded by fatty tissue, for fragmenting or aspirating undesired or pathological tissue (e.g. fatty tissue or tumors), as well as for a resection of parenchymatic organs (e.g. liver). If appropriate ultrasound applicators are available and if the power density of the ultrasound is correctly selected, the selective dissection, fragmentation, and aspiration of tissue is possible in nearly all surgical disciplines. However, two problems hinder the usability of ultrasound dissection especially in the case of endoscopic operations. This is on the one hand the missing hemostatis-effect of the ultrasound, especially during the resection of parenchymatic organs and on the other hand the lack of ability of the ultrasound to cut tissue structures containing supporting or connective tissue. These two effects not available in ultrasonic surgery are achieved very well with the RF-surgery. Therefore the combined use of ultrasonic surgery and RF-surgery allows avoiding of difficulties of the mentioned kind.

For the combined use of ultrasonic surgery and RF-surgery several techniques are available.

The easiest technique of the combined use of ultrasonic surgery and RF-surgery is, if the operating surgeon alternately uses a specific instrument for ultrasonic surgery and a different specific instrument for the RF-surgery. This technique has the advantage, that both instruments can be designed in an optimum manner for the respective purpose of use, however, also the disadvantage exists, that the change of instruments during an operation is inconvenient and very time consuming, especially in the case of endoscopic applications.

A technique known e.g. from U.S. Pat. No. 4,931,047, by which a change of instruments during an operation can be avoided, consists of applying the ultrasonic surgery and the RF-surgery by a single applicator tip of a multifunctional instrument. Thereby the ultrasound and the RF-current can be applied simultaneously or alternately. However, this technique may cause problems, since during coagulation with RF-current electric arcs or sparks may be formed between the tip of the applicator and the tissue, whereby a spark erosion and damage to the surface of the applicator tip may be caused. Furthermore, coagulated tissue may adhere to the surface of the applicator tip and hinder or even make impossible the ultrasound dissection. A further problem of this technique is to be seen in the fact, that the optimum shape of the applicator tip for ultrasound dissection is not really satisfactory for cutting with RF-current.

SUMMARY OF THE INVENTION

Accordingly, a need has arisen for improved surgical procedures and apparatus which remedy problems of the above discussed type. Therefore, it is an object of the invention to develop a multifunctional instrument, which is on the one hand appropriate for the selective dissection of biological tissue with ultrasound, and which on the other hand is appropriate for stopping of bleeding and/or for cutting of all types of tissue, even those which cannot be cut or fragmented with ultrasound.

There is, therefore, provided according to the present invention, an applicator for the ultrasonic surgery and at least one applicator for RF-surgery, e.g. for cutting and/or coagulating and/or an applicator for laser surgery in such a manner at the distal end of a combined instrument. Accordingly, ultrasound surgery as well as RF-surgery and/or the laser surgery can be used in a convenient and time saving manner without need for a change of instruments. Such combined instruments can be adapted to the respective purpose of use. As an example, a multifunctional instrument may be provided on the one hand with an applicator tip for the ultrasound dissection, which is formed and shaped in a manner adapted to the respective purpose of use and on the other hand a monopolar or bipolar hook probe can be provided, as used e.g. for the laparoscopic Cholezystektomy, for cutting and/or coagulating and stopping bleeding, by means of RF-current and/or provided with a laser probe for separating and vaporizing, of tissue structures and/or for coagulating of tissues and for stopping bleeding. Furthermore, the hook probe may be used in a known manner also for a blunt preparation of tissue.

Multifunctional instruments of this kind should be designed on the basis of ergonomics and safety conditions in such a manner, that each function can be used under conditions which are optimized as far as possible. As an example, it might be considered as useful, if each respective function to be used is available in an optimum manner. An instrument in accordance with the invention can therefore be designed in such a manner, that e.g. a hook probe usable for blunt preparation, cutting and/or coagulating is adjustable in such a manner relative to the tip of the probe of the ultrasonic applicator, such that it may have the same, or a larger or a smaller distance to the tissue, than the distal end of the ultrasonic applicator. In this manner and depending on existing demands, either the RF-current applicator (e.g. the hook probe) or the tip of the probe of the ultrasonic applicator may be moved into an optimum working position. The distal end of a laser applicator, or probe, can be fixed relative to the distal end of the ultrasonic applicator or the RF-current applicator in such a manner that the focus of the laser for cutting and for coagulating is outside the region of the distal end of the ultrasonic applicator or of the RF-current applicator, so that the ultrasonic applicator or the RF-current applicator can be used during the laser surgery as spacer or as a focussing or defocussing aid. A multifunctional instrument in accordance with the invention can also be equipped with a probe allowing argon plasma coagulation.

In addition, multifunctional instruments in accordance with the invention can be provided with devices for a suction mode and/or rinsing mode.

In a preferred embodiment multifunctional instruments in accordance with the invention may be provided with a device allowing an automatic forward movement of the RF-current applicators and/or of the laser applicators into a working position or an automatic retraction of the RF-current applicator and/or the laser applicators into a rest position, e.g. depending on enabling signals for the cutting and/or coagulation mode or for the laser or ultrasonic mode and/or for the rinsing and/or suction mode.

Other objects and advantages of the present invention will become apparent to those persons having ordinary skill in the art to which the present invention pertains from the foregoing description taken in conjunction with the accompanying drawings.

BRIEF DESCRIPTION OF THE DRAWINGS

FIGS. 1A-1D show a schematic representation of the general construction of a multifunctional instrument in accordance with the invention, for ultrasonic surgery and for RF-surgery.

FIGS. 4A-4CC show a schematic representation of an embodiment of the multifunctional instrument in accordance with the invention for ultrasonic surgery and for cutting and coagulation by means of RF-current, as well as for a blunt preparation.

FIG. 6 shows a schematic representation of an embodiment of the multifunctional instrument in accordance with the invention corresponding to the preceding embodiments, which in addition is provided with at least one device for an automatic forwarding or retracting of the RF-current applicators and/or of the laser applicator.

FIGS. 7A-7AA show a schematic representation of the suction and rinsing functions of a multifunctional instrument in accordance with the invention.

DETAILED DESCRIPTION OF DRAWINGS

Figure 2A:
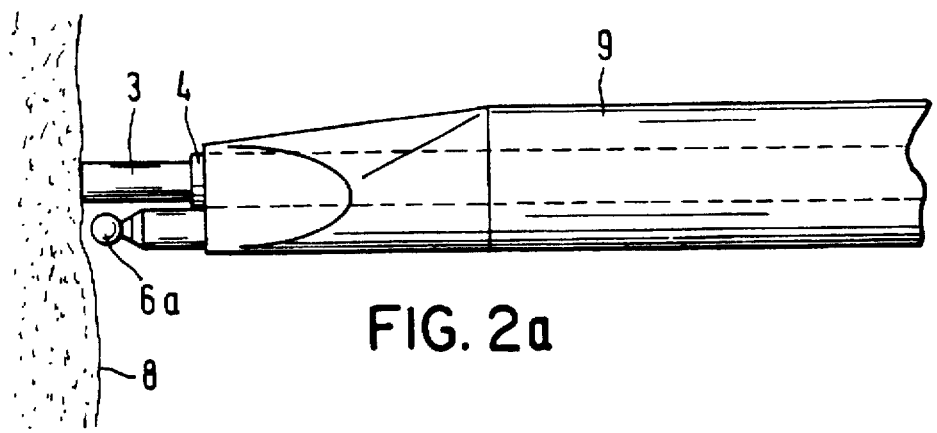
FIGS. 2A-2C show a schematic representation of an embodiment of the multifunctional instrument in accordance with the invention, for the ultrasonic surgery and for coagulation by means of RF-current through a coagulating electrode.

In FIG. 1 an embodiment of a multifunctional instrument for the ultrasonic surgery and for the RF-surgery or laser surgery is schematically shown. In the handle 1 of this instrument an electroacoustical transducer (not visible) is provided, to which the ultrasonic applicator 2 is coupled acoustically. The ultrasonic applicator comprises in a known manner an impedance transformer, the distal end 3 of which directly contacts the tissue to be fragmented or connected by a vibrating applicator tip. Specific applicator tips serve for an ergonomic and/or acoustic adaption of the distal end of the ultrasonic applicator to the respective operation method. For a laparoscopic use between the electroacoustical transducer and impedance transformer and/or between impedance transformer and applicator tip in a known manner (Cushieri) an extension piece can be connected (not shown), which transmits the ultrasound to the distal end 3 of the instrument. In the embodiment shown in FIG. 1A the impedance transformer (inclusive extension pieces, if necessary) has a rod-type construction. Surrounding the rod-type parts of the instruments a coaxial protection tube 4 may be provided, as shown in FIG. 7, the inner diameter of which is larger than the outer diameter of the rod-type parts, which tube 4 protects the rod-type parts against damaging and/or against direct contact. An embodiment of a protecting tube 4 is shown in FIG. 1D. The gap 5 shown in FIG. 7 between the rod-type parts and the protecting tube may be used in a known manner for supplying rinsing fluids. Over this protecting tube 4 an applicator device or housing 9 is arranged slidably in axial direction, which carries at its distal end at least one applicator 6, such as an electrode for cutting and/or coagulating with RF-current, or a hook electrode for blunt preparation, cutting and/or coagulating, or a probe for argon plasma coagulation. At the proximal end of the applicator device 9 a connector 11 is provided in this embodiment, to which the needed respective media like RF-current, argon and/or laser are connected. At the proximal end of the handle 1 of the ultrasound applicator 2 a connector 12 for the electroacoustical transducer, a connector 13 for suction and a connector 14 for rinsing are arranged. The connector 11 has such an ergonomic shape, that it can be used for an axial displacement of the applicator device 9 on the protecting tube 4, e.g. by means of the thumb of the hand holding the handle 1. In order to allow safe gripping, a corrugation 20 may be provided.

The applicator device 9 of the embodiment of an instrument in accordance with the invention as shown in a schematic manner in FIG. 1A, is shown in FIGS. 1B and 1C separately from two different perspectives. In an advantageous embodiment the applicator device 9 as shown in FIG. 1 is constructed in such a manner, that it can be completely removed from the ultrasonic applicator 2, so that this applicator device 9 may be combined or not with the multifunctional instrument. Furthermore this embodiment has the advantage, that depending on existing demands one of several differently complemented applicator devices can be attached to the ultrasound applicator. Embodiments of different application devices will be described below in connection with FIGS. 2 to 5.

The applicator device preferably consists of an electrically insulating material. For a supply of the RF-current from the proximal connector 11 to the several RF-current applicators 6 an electrical lead (not shown) is provided in this applicator device. For the use of argon plasma coagulation probes or laser probes the applicator device may be provided with a guiding channel (not shown), through which such probes can be inserted from the proximal to the distal end.

Figure 2B:
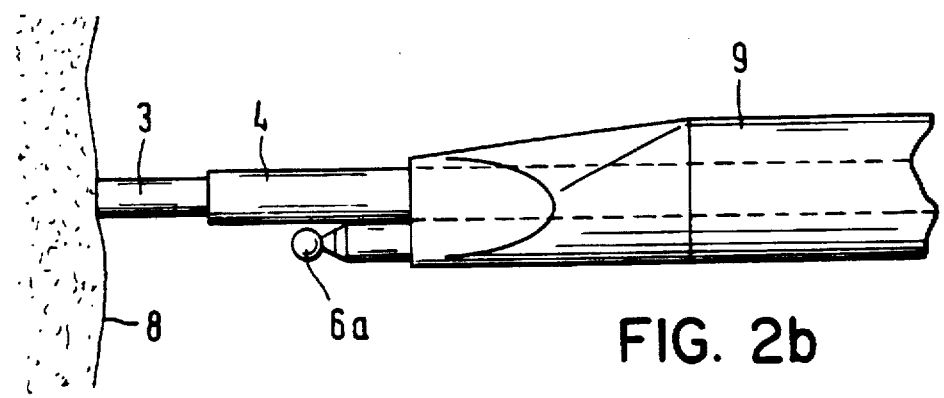
Figure 2C:
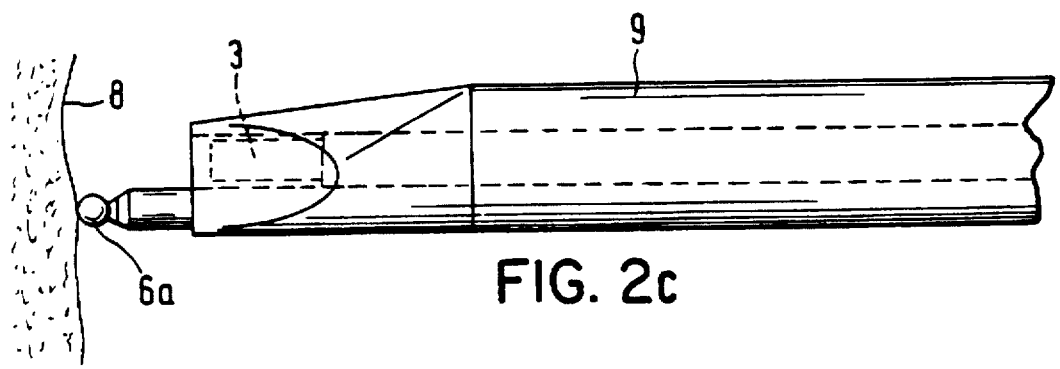

In FIG. 2 the distal end of an embodiment of a multifunctional instrument in accordance with the invention is shown which is usable for ultrasound surgery and for RF-surgery. The RF-current applicator is in this embodiment a monopolar ball-shaped coagulation electrode 6a. By an axial displacement of the applicator device 9 on the protecting tube 4 of the ultrasound applicator 2 the distal end 3 of the ultrasound applicator and the coagulation electrode 6a as shown in FIG. 2A can be positioned at the same distance to the surface 8 of the tissue or can be positioned in such a manner, that the distal end 3 of the ultrasound applicator is closer to the tissue 8 than the coagulation electrode 6a, as shown in FIG. 2B, or that the coagulation electrode 6a is closer to the tissue 8 than the distal end 3 of the ultrasound applicator 2, as shown in FIG. 2C. In this manner ultrasound dissection and RF-coagulation can be performed alternately.

Figure 3:
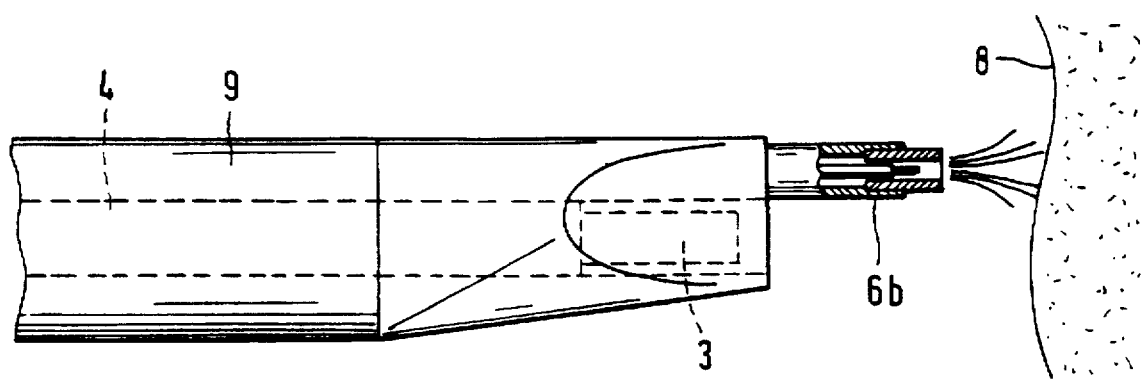
FIG. 3 shows a schematic representation of an embodiment of the multifunctional instrument in accordance with the invention for ultrasonic surgery and for coagulation by means of RF-current through an argon plasma coagulation probe.

In FIG. 3 an embodiment in accordance with the invention is shown, which is usable for ultrasound surgery and RF-surgery. The RF-current applicator is in this embodiment an argon plasma coagulation probe 6b. By an axial displacement of the applicator device 9 on the protecting tube 4 of the ultrasound applicator 2 the distal end 3 of the ultrasound applicator and the argon plasma coagulation probe 6b can be positioned at the same distance to the surface 8 of the tissue, or can be positioned in such a manner, that the distal end 3 of the ultrasound applicator is closer to the tissue 8 than the argon plasma coagulation probe 6b, or can be positioned in such a manner, that the probe 6b is closer to the tissue 8 than the distal end 3 of the ultrasound applicator 2. The mentioned positions are not shown in FIG. 3, since they principally correspond to the positions as shown in FIGS. 2 and 4. In this manner ultrasound dissection and argon plasma coagulation can be performed alternately.

Figure 5:
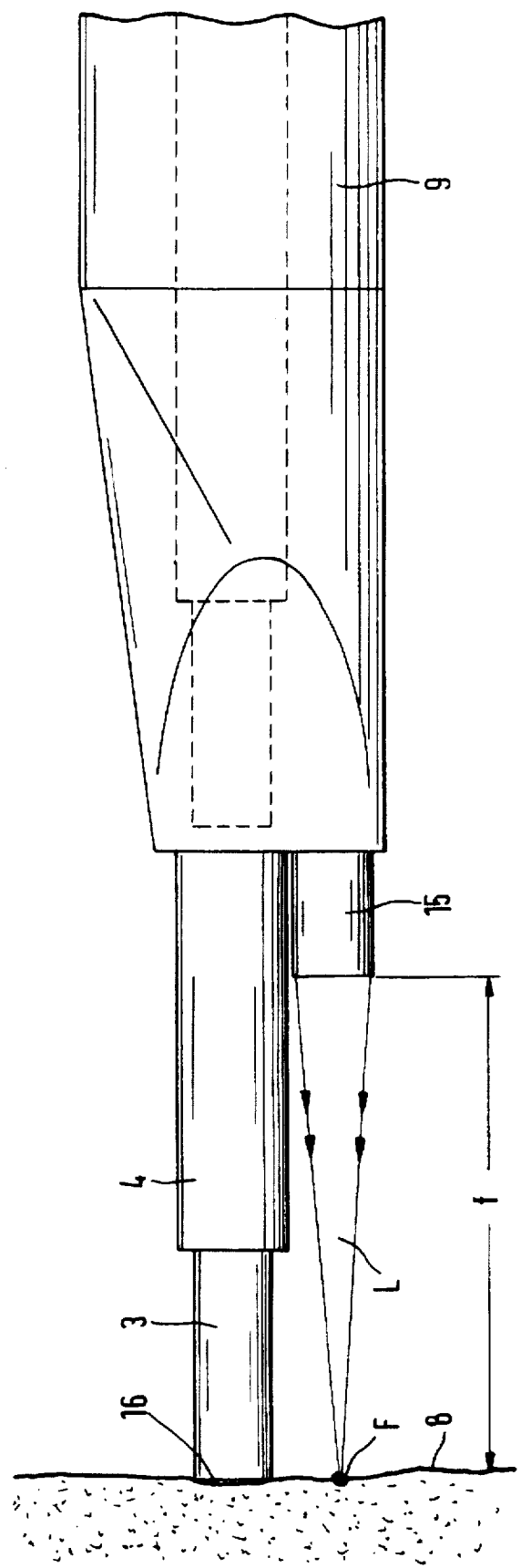
FIG. 5 shows a schematic representation of an embodiment of the multifunctional instrument in accordance with the invention for the ultrasonic surgery, which is provided with a laser probe for cutting or coagulating.

FIG. 4 shows a schematic representation of a multifunctional instrument for ultrasound surgery and for RF-surgery. The RF-current applicator is in this embodiment a hook probe 6c, which is used as an example for the laparoscopic Cholezystektomy. By an axial displacement of the applicator device 9 on the tube 4 of the ultrasound applicator 2 the distal end 3 of the ultrasound applicator 2 and of the hook probe 6c can be positioned in the same distance to the tissue 8 as shown in FIG. 2A, or can be positioned in such a manner, that the distal end of the ultrasound applicator is closer to the tissue 8 than the hook probe 6c, as shown in FIGS. 4B and 4BB, or the hook probe 6c can be positioned to be closer to the tissue 8 than the distal end 3 of the ultrasound applicator 2, as shown in FIGS. 4C and 4CC. In this manner ultrasound dissection and blunt preparation or cutting and/or coagulation with RF-current can be used alternately. FIG. 5 shows a schematic representation of a multifunctional instrument in accordance with the invention, for the ultrasound surgery and for laser surgery. The laser probe 15 is inserted from the proximal to the distal end through the applicator device 9 and is fixed in the applicator device 9. By an axial displacement of the applicator device 9 to the proximal end on the tube 4 of the ultrasound applicator 2 the laser probe 15 can be arranged in such a distance f to the tissue 8, that the focus F of the laser L lies in the plane of the contact surface 16 of the distal ends 3 of the ultrasound applicator 2. In this manner the distal end 3 of the ultrasound applicator 2 can be used as spacer for the laser application, in order to perform an evaporation of tissue or to separate tissue. If the applicator device or housing 9 with the laser probe 15 is moved out of this position to the proximal or to the distal end on the tube 4 of the ultrasound applicator, the laser L on the surface of the tissue is defocussed and therefore the power density is reduced to provide a coagulation effect instead of a vaporization effect.

FIG. 6 shows a schematic representation of an embodiment of a multifunctional instrument in accordance with the invention corresponding to the above described embodiments, but being further provided with a device 17 for an automatic advance or retraction of the applicator device 9 with the respective RF-current applicator and/or laser applicator. This device 17 is called controller in the following description. The controller can work e.g. in an electromagnetic, pneumatic or hydraulic manner. Such controllers are known, see, e.g., G. Farin: Pneumatically controlled Bipolar Cutting Instrument, in Endoscopic Surgery and Allied Technologies, Issue 2, 1993, pages 97–101, Editor Thieme Stuttgart, the disclosure of which is incorporated by reference. Advancing or retracting of the applicator device can be caused automatically by the enabling signals of the respective instrument connected to the RF-electrosurgical apparatus, laser apparatus or ultrasound apparatus. As an example, an enabling signal "cut with RF-current" can cause the hook electrode as shown in FIG. 4C to be automatically advanced into the working position. As an example, the controller may be arranged at or in the handle 1 of the instrument.

The embodiment shown in FIG. 6 serves for illustrating the principle of the automatic advance of the RF-surgery applicators or the laser applicators relative to the ultrasound applicator. This advancing of the RF-surgery applicators or the laser applicators relative to the ultrasound applicator can also be realized in a different manner, e.g. in such a manner that the applicator device is a fixed or replaceable component of the instrument in accordance with the invention, whilst the RF-surgery applicators or the laser applicators can be moved manually or automatically by means of controllers relative to the ultrasound applicator.

FIG. 7 shows a detailed representation of a suction function and rinsing function of the instrument, which functions are known as such. In this embodiment besides an RF-current applicator 10 of any desired kind an ultrasound applicator is provided, which is shaped as a tube having a lumen 18 from the distal end 3 to the connector 14 which can be used as a suction channel. The gap 5 between the ultrasound applicator 2 and the protection tube 4 which can be used for rinsing, has already been described.

In the shown and described embodiments an adjustability of the applicators by a movement in a longitudinal direction is provided. However, in certain cases it is advantageous to provide the applicator in a revolver unit, which can be rotated around its longitudinal axis and is mounted at the instrument. If as an example three applicators are provided and if at first the distal end 3 of the ultrasound applicator is in the working position, the distal end of another applicator can be automatically moved into the same working position, by retracting first the first applicator, whereafter the revolver unit is rotated in such a manner, that the second or third applicator is moved after an appropriate advance for achieving a predetermined distance to the tissue into an appropriate working position, whereby the instrument as such need not be moved. As in the case of the mentioned known pneumatically controlled multifunctional instrument, the control unit for the embodiments of the invention can contain a logic circuitry with a microprocessor, having a program allowing the automatic adjustments for the provided functions.

We claim:

1. A multifunctional surgical instrument, comprising:
   an instrument housing having distal and proximal ends;
   an ultrasonic cutting tool extending longitudinally through said housing and having a tool tip extending from said distal end of said housing;
   an electrosurgical coagulating tool extending longitudinally through said housing and having a tool tip extending from said distal end of said housing;
   said ultrasonic cutting tool tip and said electrosurgical coagulating tool tip being laterally spaced apart;

said ultrasonic cutting tool and said electrosurgical coagulating tool being longitudinally movable in said housing, whereby said ultrasonic cutting tool tip and said electrosurgical coagulating tool tip may be separately retracted or extended to be positioned relative to a tissue to be treated using said surgical instrument;

wherein said housing includes an electrical insulating material whereby said ultrasonic cutting tool is electrically insulated from said electrosurgical coagulating tool.

2. A multifunctional surgical instrument in accordance with claim 1, further comprising channels extending through said housing from distal ends adjacent said tool tips to provide suction and rinsing fluid to an area adjacent said tool tips.

3. A multifunctional surgical instrument in accordance with claim 1, wherein said electrosurgical coagulating tool comprises an RF current applicator capable of cutting and coagulating tissue.

4. A multifunctional surgical instrument in accordance with claim 3, wherein said electrosurgical coagulating tool comprises a monopolar coagulation electrode.

5. A multifunctional surgical instrument in accordance with claim 4, wherein said electrosurgical coagulating tool is shaped as a manipulation hook for use in cholezystektomy.

6. A multifunctional surgical instrument in accordance with claim 1, wherein said electrosurgical coagulating tool comprises an argon plasma coagulation probe.

7. A multifunctional surgical instrument in accordance with claim 1, wherein said electrosurgical coagulating tool comprises a laser applicator.

8. A multifunctional surgical instrument in accordance with claim 1, wherein said housing is provided with a controller for automatically adjusting the longitudinal position of the ultrasonic cutting tool tip to a predetermined position relative to the electrosurgical coagulating tool tip.

9. A multifunctional surgical instrument in accordance with claim 1, wherein said ultrasound cutting tool and said electrosurgical coagulating tool are rotatable within said housing to permit successive use of each tool at a same position relative to a tissue without adjustment of said housing.

10. A multifunctional surgical instrument, comprising:

an instrument housing having distal and proximal ends;

an ultrasonic cutting tool extending longitudinally through said housing and having a tool tip extending from said distal end of said housing;

an RF electrosurgical tool extending longitudinally through said housing and having a tool tip extending from said distal end of said housing;

said ultrasonic cutting tool tip and said RF electrosurgical tool tip being laterally spaced apart;

said ultrasonic cutting tool and said RF electrosurgical tool being longitudinally movable in said housing, whereby said ultrasonic cutting tool tip and said RF electrosurgical tool tip may be separately retracted or extended to be positioned relative to a tissue to be treated using said surgical instrument; and an electrical insulating material in said housing electrically insulating said ultrasonic cutting tool from said RF electrosurgical tool.

11. A multifunctional surgical instrument in accordance with claim 10, wherein said housing is provided with a controller for automatically adjusting the longitudinal position of the ultrasonic cutting tool tip to a predetermined position relative to the RF electrosurgical tool tip.

12. A multifunctional surgical instrument in accordance with claim 10, wherein said ultrasound cutting tool and said RF electrosurgical tool are rotatable within said housing to permit successive use of each tool at a same position relative to a tissue without adjustment of said housing.

13. A multifunctional surgical instrument in accordance with claim 10, further comprising channels extending through said housing from distal ends adjacent said tool tips to provide suction and rinsing fluid to an area adjacent said tool tips.

14. A multifunctional surgical instrument, comprising:

an instrument housing having distal and proximal ends;

an ultrasonic cutting tool extending longitudinally through said housing and having a tool tip extending from said distal end of said housing;

an electrosurgical coagulating tool extending longitudinally through said housing and having a tool tip extending from said distal end of said housing;

said ultrasonic cutting tool tip and said electrosurgical coagulating tool tip being laterally spaced apart, wherein said ultrasonic cutting tool and said electrosurgical coagulating tool are longitudinally movable in said housing, whereby said ultrasonic cutting tool tip and said electrosurgical coagulating tool tip may be separately retracted or extended to be positioned relative to a tissue to be treated using said surgical instrument, and wherein said ultrasound cutting tool and said electrosurgical coagulating tool are rotatable within said housing to permit successive use of each tool at a same position relative to a tissue without adjustment of said housing.

15. A multifunctional surgical instrument in accordance with claim 14, wherein said housing is provided with a controller for automatically adjusting the longitudinal position of the ultrasonic cutting tool tip to a predetermined position relative to the electrosurgical coagulating tool tip.

16. A multifunctional surgical instrument, comprising:

an instrument housing having distal and proximal ends;

an ultrasonic cutting tool extending longitudinally through said housing and having a tool tip extending from said distal end of said housing;

an electrosurgical tool extending longitudinally through said housing and having a tool tip extending from said distal end of said housing;

said ultrasonic cutting tool tip and said electrosurgical tool tip being laterally spaced apart;

said ultrasonic cutting tool and said electrosurgical tool being longitudinally movable in said housing, whereby said ultrasonic cutting tool tip and said electrosurgical tool tip may be separately retracted or extended to be positioned relative to a tissue to be treated using said surgical instrument; wherein said housing includes an electrical insulating material whereby said ultrasonic cutting tool is electrically insulated from said electrosurgical coagulating tool; and wherein said housing is provided with a controller for automatically adjusting the longitudinal position of the ultrasonic cutting tool tip to a predetermined position relative to the RF electrosurgical tool tip.

17. A multifunctional surgical instrument in accordance with claim 16, further comprising channels extending through said housing from distal ends adjacent said tool tips to provide suction and rinsing fluid to ah area adjacent said tool tips.

* * * * *